United States Patent
Kawakami et al.

(10) Patent No.: US 6,780,623 B1
(45) Date of Patent: Aug. 24, 2004

(54) LOW TEMPERATURE EXPRESSION CDNAS ENCODING FRUCTAN SYNTHESIZING ENZYMES AND METHOD OF ISOLATING THE SAME

(75) Inventors: Akira Kawakami, Hokkaido (JP); Midori Kuriki, Hokkaido (JP); Fumihiro Terami, Hokkaido (JP)

(73) Assignee: National Agricultural Research Organization (NARO), Ibaraki (JP)

( * ) Notice: Subject to any disclaimer, the term of this patent is extended or adjusted under 35 U.S.C. 154(b) by 0 days.

(21) Appl. No.: 09/534,228

(22) Filed: Mar. 24, 2000

(30) Foreign Application Priority Data

Mar. 25, 1999 (JP) ............................................ 11-081695

(51) Int. Cl.[7] .................................................. C12N 9/10
(52) U.S. Cl. .................... 435/193; 435/183; 435/252.3; 435/254.2; 435/320.1; 536/23.2
(58) Field of Search ................................ 435/183, 193, 435/252.3, 254.2, 320.1; 535/23.2

(56) References Cited

PUBLICATIONS

Sprenger et al. Accession X83233. Jun. 5, 1998.*

* cited by examiner

*Primary Examiner*—Ponnathapu Achutamurthy
*Assistant Examiner*—Christian L Fronda
(74) *Attorney, Agent, or Firm*—Arent Fox Kintner Plotkin & Kahn, PLLC

(57) ABSTRACT

A wheat-derived sucrose:fructan 6-fructosyltransferase cDNA is provided which is characterized in that said cDNA has a nucleotide sequence corresponding to an amino acid sequence listed as SEQ.ID. No. 1 in FIG. 1. A wheat-derived invertase cDNA is provided which is characterized in that said cDNA has a nucleotide sequence corresponding to an amino acid sequence listed as SEQ.ID. No. 2 in FIG. 2. A method is provided for isolating a wheat-derived sucrose:fructan 6-fructosyltransferase cDNA having a nucleotide sequence corresponding to an amino acid sequence listed as SEQ.ID. No.1 in FIG. 1 and a wheat-derived invertase cDNA having a nucleotide sequence corresponding to an amino acid sequence listed as SEQ.ID. No. 2 in FIG. 2.

4 Claims, 2 Drawing Sheets

FIG.1

AMINO ACID SEQUENCE OF SEQ. ID No1.

```
              10         20         30         40         50         60
        MGSHGKPPLP YAYKPLPSDA DGERAGCTRW RVCAVALTAS AMVVVVVGAT LLAGFRVDQA
              70         80         90        100        110        120
        VDEEAAGGFP WSNEMLQWQR SGYHFQTAKN YMSDPNGLMY YRGWYHMFFQ YNPVGTDWDD
             130        140        150        160        170        180
        GMEWGHAVSR NLVQWRTLPI AMVADQWYDI LGVLSGSMTV LPNGTVIMIY TGATNASAVE
             190        200        210        220        230        240
        VQCIATPADP TDPLLRRWTK HPANPVIWSP PGVGTKDFRD PMTAWYDESD DTWRTLLGSK
             250        260        270        280        290        300
        DDNNGHHDGI AMMYKTKDFL NYELIPGILH RVERTGEWEC IDFYPVGRRT SDNSSEMLHV
             310        320        330        340        350        360
        LKASMDDERH DYYSLGTYDS AANRWTPIDP ELDLGIGLRY DWGKFYASTS FYDPAKKRRV
             370        380        390        400        410        420
        LMGYVGEVDS KRADVVKGWA SIQSVPRTIA LDEKTRTNLL LWPVEEIETL RLNATELSDV
             430        440        450        460        470        480
        TLNTGSVIHI PLRQGTQLDI EATFHLDASA VAALNEADVG YNCSSSGGAV NRGALGPFGL
             490        500        510        520        530        540
        LVLAAGDRRG EQTAVYFYVS RGLDGGLHTS FCQDELRSSR AKDVTKRVIG STVPVLDGEA
             550        560        570        580        590        600
        FSMRVLVDHS IVQGFAMGGR TTMTSRVYPM EAYQEAKVYL FNNATGASVT AERLVVHEMD
             610        620        630        640        650        660
        SAHNQLSNMD DHSYVQ*... .......... .......... .......... ..........
```

FIG. 2

AMINO ACID SEQUENCE OF SEQ. ID No2.

```
         10         20         30         40         50         60
  MDSSRVILIP GTPPLPYAYE QLPSSSADAK GIEEERAGGG GLRWRACAAV LAASAVVALV 70         80         90        100        110        120
  VAAAVFGASG AGWDAVAASV PATPATEFPR SRGKEHGVSE KTSGAYSANA FPWSNAMLQW 130        140        150        160        170        180
  QRTGYHFQPD KYYQNDPNGP VYYGGWYHFF YQYNPSGSVW EPQIVWGHAV SKDLIHWRHL 190        200        210        220        230        240
  PPALVPDQWY DIKGVLTGSI TVLPDGKVIL LYTGNTETFA QVTCLAEPAD PSDPLLREWV 250        260        270        280        290        300
  KHPANPVVFP PPGIGMKDFR DPTTAWFDES DGTWRTIIGS KNDSDHSGIV FSYKTKDFLS 310        320        330        340        350        360
  YELMPGYMYR GPKGTGEYEC IDLYAVGGGR KASDMYNSTA EDVLYVLKES SDDDRHDWYS 370        380        390        400        410        420
  LGRFDAAANK WTPIDEELEL GVGLRYDWGK YYASKSFYDP VKKRRVVWAY VGETDSERAD 430        440        450        460        470        480
  ITKGWANLQS IPRTVELDEK TRTNLVQWPV EELDALRINT TDLSGITVGA GSVAFLPLHQ 490        500        510        520        530        540
  TAQLDIEATF RIDASAIEAL NEADVSYNCT TSSGAATRGA LGPFGLLVLA NRALTEQTGV 550        560        570        580        590        600
  YFYVSKGLDG GLRTHFCHDE LRSSHASDVV KRVVGSTVPV LDGEDFSVRV LVDHSIVQSF 610        620        630        640        650        660
  AMGGRLTATS RAYPTEAIYA AAGVYMFNNA TGTSVTAEKL VVHDMDSSYN HIYTDDDLVV 670        680        690        700        710        720
  VD*....... .......... .......... .......... .......... ..........
```

US 6,780,623 B1

LOW TEMPERATURE EXPRESSION CDNAS ENCODING FRUCTAN SYNTHESIZING ENZYMES AND METHOD OF ISOLATING THE SAME

BACKGROUND OF THE INVENTION

The present invention relates to low temperature expression cDNAs encoding fructan synthesizing enzymes and a method of isolating the same. In detail, this invention relates to cDNAs encoding enzymes effective for synthesizing a fructan which is useful for improving cold resistance of plants and can serve as a fructo-oligosaccharide useful for improving human's health. In particular, this invention relates to the provision of a novel sucrose:fructan 6-fructosyltransferase cDNA isolated from a winter wheat (PI173438) having high freezing tolerance and a novel invertase cDNA isolated from the same winter wheat (PI173438).

It has been known that wintering crops such as wheats and forage grasses will acquire a freezing tolerance induced during a cold acclimation from autumn to winter. Further, it has been found that these wintering crops have fructan synthesizing enzymes which will express under a low temperature during cold acclimation, and as a result, polysaccharide fructan will be synthesized and accumulated as an energy source within vacuoles of these crops. Since wintering crops are often planted in severely cold areas, it is desired that the fructan be accumulated as large amount as possible.

Moreover, it has been found that the fructan can serve not only as an energy source for a plant to live through a severe winter, but also can serve to prevent a plant from freezing and to adjust the osmotic pressure of a plant so as to prevent it from desiccation.

Recently, some new wheat varieties have been developed in some northern countries, but it has been proved difficult to obtain a new wheat variety having more improved capabilities than those of existing ones, if we only use a conventional hybridization technique. For this reason, there has been a demand that research and development of a new wheat variety be conducted by means of gene engineering.

On the other hand, fructan can serve as a fructo-oligosaccharide which has been proved useful for preventing a carious tooth and for increasing intestinal bifid bacteria (useful for improving human health). In fact, a cDNA encoding fructan synthesizing enzyme (it may also be referred to as fructan synthesizing cDNA) is useful for producing the fructo-oligosaccharide at an industrial level.

In detail, enzymes capable of synthesizing fructan may be classified into several species and can have several isozymes in view of different reaction stages and different combined states. In more detail, sucrose:fructan 6-fructosyltransferase is mainly useful for synthesizing a trisaccharide or a tetracharide using sucrose as starting substance and for extending a degree of fructose polymer using fructan. Invertase can usually serve as an enzyme for decomposing the sucrose (disaccharide). Further, invertase of plants possessing a fructan accumulation ability (such plants include wheat and forage grasses) may be used to synthesize a trisaccharide in the presence of a high concentration sucrose.

It is reported that the sucrose:fructan 6-fructosyltransferase cDNA may be isolated from barley, while the invertase cDNA may be isolated from several other kinds of plants. However, since these cDNAs are all isolated under a condition suitable for cDNAs to express at the room temperature, it is not sure whether they can express at a low temperature and hence they may not have a function as an enzyme under a low temperature environment. As a result, the conventional fructan 6-fructosyltransferase cDNA and the conventional invertase cDNA can not be used to improve the cold resistance of a plant.

SUMMARY OF THE INVENTION

It is an object of the present invention to provide cDNAs encoding fructan synthesizing enzymes capable of expressing under a low temperature environment, which cDNAs are isolated from a winter wheat (PI173438) having a high freezing tolerance.

It is another object of the present invention to provide cDNAs encoding fructan synthesizing enzymes useful for industrially producing fructo-oligosaccharides which are useful for preventing a carious tooth and for increasing intestinal bifid bacteria.

It is a further object of the present invention to provide a method for isolating the above cDNAs capable of expressing in a low temperature environment.

According to one aspect of the present invention, there is provided a wheat-derived sucrose:fructan 6-fructosyltransferase cDNA, characterized in that said cDNA has a nucleotide sequence corresponding to an amino acid sequence listed as SEQ.ID. No.1 in FIG. 1. In detail, said cDNA comprises 1848 nucleotides/616 amino acids and has 93% identity (on amino acid sequence level) with barley-derived sucrose:fructan 6-fructosyltransferase cDNA. In more detail, said cDNA encodes a fructan synthesizing enzyme in a low temperature environment and can confer a cold resistance to a plant upon being introduced into the plant. In further detail, said cDNA encodes an enzyme having a function of synthesizing a fructo-oligosaccharide useful for improving human's health.

According to one aspect of the present invention, there is provided a wheat-derived invertase cDNA, characterized in that said cDNA has a nucleotide sequence corresponding to an amino acid sequence listed as SEQ.ID. No.2 in FIG. 2. In detail, said cDNA comprises 1986 nucleotides/662 amino acids and has 55% identity (on amino acid sequence level) with sugarcane-derived invertase cDNA. In more detail, said cDNA encodes a fructan synthesizing enzyme in a low temperature environment and can confer a cold resistance to a plant upon being introduced into the plant. In further detail, said cDNA encodes an enzyme having a function of synthesizing a fructo-oligosaccharide useful for improving human's health.

According to a further aspect of the present invention, there is provided a method of isolating a wheat-derived sucrose:fructan 6-fructosyltransferase cDNA having a nucleotide sequence corresponding to an amino acid sequence listed as SEQ.ID. No.1 in FIG. 1 and a wheat-derived invertase cDNA having a nucleotide sequence corresponding to an amino acid sequence listed as SEQ.ID. No.2 in FIG. 2, said method comprising the steps of: extracting mRNA from winter wheat variety PI173438 (having a high freezing tolerance) that has undergone a sufficient cold acclimation; preparing cDNA and a cDNA library based on said mRNA; analyzing nucleotide sequences of a number of plant-derived sucrose:fructan 6-fructosyltransferase cDNAs and plant-derived invertase cDNAs which have all been published by EMBL/Genebank/DDBJDNA Databank; designing a pair of (sucrose:fructan 6-fructosyltransferase and invertase) cDNA-specific degenerated primers with reference to highly conserved nucleotide sequence portions of the sucrose:fructan 6-fructosyltransferase cDNAs and the invertase cDNAs; conducting PCR (polymerase chain reaction) using the pair of (sucrose:fructan 6-fructosyltransferase and invertase) cDNA-specific degenerated primers and using said cDNA as a template, thereby amplifying fragments of sucrose:fructan 6-fructosyltransferase cDNA and invertase cDNA and obtaining amplified DNA fragments; and using said amplified DNA fragments as probes for screening said cDNA library by a hybridization assay, to isolate recombinant plaques containing full length of cDNA.

In the method of the present invention, one of (sucrose:fructan 6-fructosyltransferase and invertase) cDNA-specific degenerated primers has the following nucleotide sequence:

(Forward): 5' A-T-G-A-A-T/C-G-A-T/C-C-C-N-A-A-T/C-G-G (SEQ.ID. No.3)

and the other has the following nucleotide sequence:

(Reverse): 5' C-C-N-G-T-N-G-C-A/G-T-T-A/G-T-T-A-/G-A-A (SEQ.ID. No.4).

The above objects and features of the present invention will become better understood from the following description with reference to the accompanying drawings.

BRIEF DESCRIPTION OF DRAWINGS

FIG. 1 shows an amino acid sequence of SEQ.ID No.1.

FIG. 2 shows an amino acid sequence of SEQ.ID No.2.

DETAILED DESCRIPTION OF THE PREFERRED EMBODIMENTS

The cDNAs of the present invention are those encoding fructan synthesizing enzymes capable of expressing at low temperature environment.

The isolation method for isolating the above cDNAs of the present invention may be carried out in the following manner.

Specifically, mRNA is extracted from winter wheat PI173438 (having a high freezing tolerance) that has undergone a cold acclimation under natural conditions in Sapporo City Japan until November 22. This mRNA is then used to prepare cDNA and a cDNA library.

Next, nucleotide sequences of a number of plant-derived sucrose:fructan 6-fructosyltransferase cDNAs and invertase cDNAs which have all been published by EMBL/Genebank/DDBJDNA Databank are closely analyzed, and a pair of cDNA-specific degenerated primers (capable of simultaneously amplifying both the sucrose:fructan 6-fructosyltransferase cDNA and invertase cDNA) are designed with reference to highly conserved nucleotide sequence portions.

The pair of designed (sucrose:fructan 6-fructosyltransferase and invertase) cDNA-specific degenerated primers are used in a PCR (polymerase chain reaction) using the above-mentioned cDNA as the template for amplifying the expected sucrose:fructan 6-fructosyltransferase cDNA fragments and invertase cDNA fragments (both are approximately 1500 bp), and the amplified fragments are isolated.

The amplified fragments are used as probes for screening the cDNA library by a hybridization assay, to isolate recombinant plaques containing full length of cDNA. The nucleotide sequences of the isolated plagues were analyzed and demonstrated to be two different isolated cDNAs which are sucrose:fructan 6-fructosyltransferase cDNA fragments and invertase cDNA fragments, all are novel in plants.

An example of the method for isolating the cDNAs of the present invention was carried out in the following steps 1)–3).

1) Preparation of cDNA and cDNA Library from Freezing Tolerance Winter Wheat Variety PI173438 mRNA was extracted by a common method from the crown portion of winter wheat (*Triticum astivum* L.) PI173438 (having high freezing tolerance) that had been seeded in a container in late September and had then undergone a cold acclimation under natural conditions until November 22. A portion (5 µg) of the obtained mRNA was used to synthesize cDNA utilizing a cDNA Synthesis Kit (STRATAGENE Co.). After attaching adaptors to both ends of the cDNA, it was incorporated into a ZAP Expression Vector (STRATAGENE Co.), thereby obtaining a cDNA library of approximately $6 \times 10^6$ pfu.

2) PCR Reaction Using a Pair of (Sucrose:fructan 6-fructosyltransferase and Invertase) cDNA-specific Degenerated Primers and Using the cDNA as a Template One of the pair of (sucrose:fructan 6-fructosyltransferase and invertase) cDNA-specific degenerated primers having the following nucleotide sequence:

(Forward): 5' A-T-G-A-A-T/C-G-A-T/C-C-C-N-A-A-T/C-G-G (SEQ.ID. No.3)

the other of the pair of (sucrose:fructan 6-fructosyltransferase and invertase) cDNA-specific degenerated primers, having the following nucleotide sequence:

(Reverse): 5' C-C-N-G-T-N-G-C-A/G-T-T-A/G-T-T-A-/G-A-A (SEQ.ID. No.4), both of which were synthesized based on highly conserved regions of the nucleotide sequences of known sucrose:fructan 6-fructosyltransferase cDNA and invertase cDNA (published by EMBL/Genebank/DDBJDNA Databank), were used in a PCR using the cDNA (synthesized in the manner described in the above) as the template.

The PCR reaction was performed in a final volume of 50 µl. In detail, 1 µl of Taq DNA polymerase (5 units/µl) by Nippon Gene Co., 5 µl of 10×PCR buffer (containing $MgCl_2$), 5 µl of dNTP solution (10 mM), 2 µl of each primer (12 µM) and about 10 ng of the cDNA synthesized in the above, were mixed and then brought to a total of 50 µl with distilled water. The PCR condition and number of reaction cycles are shown in Table 1 below.

TABLE 1

| PCR Conditions and Number of Reaction Cycles | | | |
|---|---|---|---|
| Initial Denaturation | 94° C. | 1 min | once |
| Denaturation | 94° C. | 1 min | 30 cycles |
| Annealing | 50° C. | 1 min | |
| Primer Extension | 72° C. | 2 min | |
| Final Extension | 72° C. | 2 min | once |

(In Table 1, "denaturation" refers to a reaction in which double-stranded DNA is melt into single strand and secondary structure is eliminated, "primer extension" refers to an synthesizing of the new complementary strand, and "30 cycles" means that three basic steps of denaturation-annealing-primer extension are repeated with 30 cycles.

As a result, DNA fragments (having expected length of approximately 1500 bp) of (sucrose:fructan 6-fructosyltransferase and invertase) cDNAs were amplified by the above PCR with the pair of (sucrose:fructan 6-fructosyltransferase and invertase) cDNA-specific degenerated primers having nucleotide sequence of SEQ.ID No.3 and nucleotide sequence of SEQ.ID No.4. Theses amplified DNA fragments were then isolated and subsequently sequenced using a DNA sequencer (Model 373S by ABI Co.) according to a conventional method. By comparing the sequences with known sucrose:fructan 6-fructosyltransferase cDNA and know invertase cDNA, it were confirmed that novel sucrose:fructan 6-fructosyltransferase cDNA fragments and novel invertase cDNA fragments were isolated.

3) Isolation and Nucleotide Sequencing of Full Length of cDNAs Encoding Sucrose:fructan 6-fructosyltransferase and Invertase of the Present Invention About 1×10$^5$ recombinant plagues from the cDNA library obtained in the manner described in the above were subjected to a hybridization assay by using filters lifted with 1×10$^5$ recombinant plaques, and using probes prepared by labeling (with $^{32}$P) each novel (sucrose:fructan 6-fructosyltransferase and invertase) cDNA fragment obtained in the above.

The hybridization reaction was carried out for 16 hours at 42° C., in a solution containing 50% formamide, 5×SSPE, 5×Denhardt's solution, 0.5% SDS and 0.2 mg/ml salmon sperm DNA with $^{32}$P-labeled each probe.

The filters were then washed twice in a solution containing 2×SSC and 0.1% SDS at 65° C. for 10 min. Afterwards, the filters were washed twice with another washing solution containing 0.1×SSC and 0.1% SDS, at 65° C. for 15 min. Detection of each positive plaque binding to $^{32}$P-labeled probe was performed by exposing above washed filters to X-ray films.

About 35 positive recombinant plaques obtained in the above were subjected to nucleotide sequencing with DNA Sequencer by ABI Co. Analysis of the nucleotide sequences of these recombinant plaques revealed that novel sucrose:fructan 6-fructosyltransferase cDNA having a nucleotide sequence corresponding to the amino acid sequence listed as SEQ.ID No. 1 in FIG. 1 and novel invertase cDNA having a nucleotide sequence corresponding to the amino acid sequence listed as SEQ.ID No. 2 in FIG. 2 had been isolated from the winter wheat.

In fact, what were isolated were i) a novel wheat-derived sucrose:fructan 6-fructosyltransferase cDNA having a nucleotide sequence corresponding to the amino acid sequence listed as SEQ.ID. No.1 in FIG. 1, comprising 1848 nucleotides/616 amino acids and having 93% identity (on amino acid sequence level) with barley-derived sucrose:fructan 6-fructosyltransferase cDNA, ii) a novel wheat-derived invertase cDNA having a nucleotide sequence corresponding to the amino acid sequence listed as SEQ.ID. No.2 in FIG. 2, comprising 1986 nucleotides/662 amino acids and having 55% identity (on amino acid sequence level) with sugarcane-derived invertase cDNA.

Investigation of Enzymatic Activity

In order to investigate enzymatic activities of the novel wheat-derived sucrose:fructan 6-fructosyltransferase cDNA and the novel wheat-derived invertase cDNA of the present invention, enzymatic reactions were conducted under the following conditions with the use of culture solutions containing the novel proteins secreted by recombinant yeast (into which novel sucrose:fructan 6-fructosyltransferase cDNA and the novel invertase cDNA of the present invention have been introduced).

[Enzymatic Reaction Condition]

Buffer solution (20 mM citric acid/phosphoric acid), pH 5.5

Final substrate concentration: 50 mM sucrose

Reaction temperature: 4° C., reaction time: 17 hours.

As a result, it was confirmed that a culture solution containing novel protein secreted by recombinant yeast (into which novel sucrose:fructan 6-fructosyltransferase cDNA of the present invention has been introduced), had a function of synthesizing a kestotriose (a trisaccharide) and a kestotetraose (a tetrasaccharide) using sucrose (disaccharide) as a substrate. Also, it was confirmed that a culture solution containing novel protein secreted by recombinant yeast (into which novel invertase cDNA of the present invention has been introduced), had a function of synthesizing a kestotriose (a trisaccharide) using sucrose (disaccharide) as a substrate.

The nucleotide sequences of the novel cDNAs obtained in the present invention are listed in the following.

SEQUENCE LISTING

<160> NUMBER OF SEQ ID NOS: 6

<210> SEQ ID NO 1
<211> LENGTH: 616
<212> TYPE: PRT
<213> ORGANISM: Triticum aestivum

<400> SEQUENCE: 1

```
Met Gly Ser His Gly Lys Pro Pro Leu Pro Tyr Ala Tyr Lys Pro Leu
1               5                   10                  15

Pro Ser Asp Ala Asp Gly Glu Arg Ala Gly Cys Thr Arg Trp Arg Val
            20                  25                  30

Cys Ala Val Ala Leu Thr Ala Ser Ala Met Val Val Val Val Val Gly
        35                  40                  45

Ala Thr Leu Leu Ala Gly Phe Arg Val Asp Gln Ala Val Asp Glu Glu
    50                  55                  60
```

-continued

```
Ala Ala Gly Gly Phe Pro Trp Ser Asn Glu Met Leu Gln Trp Gln Arg
65                  70                  75                  80

Ser Gly Tyr His Phe Gln Thr Ala Lys Asn Tyr Met Ser Asp Pro Asn
                85                  90                  95

Gly Leu Met Tyr Tyr Arg Gly Trp Tyr His Met Phe Phe Gln Tyr Asn
            100                 105                 110

Pro Val Gly Thr Asp Trp Asp Gly Met Glu Trp Gly His Ala Val
        115                 120                 125

Ser Arg Asn Leu Val Gln Trp Arg Thr Leu Pro Ile Ala Met Val Ala
    130                 135                 140

Asp Gln Trp Tyr Asp Ile Leu Gly Val Leu Ser Gly Ser Met Thr Val
145                 150                 155                 160

Leu Pro Asn Gly Thr Val Ile Met Ile Tyr Thr Gly Ala Thr Asn Ala
                165                 170                 175

Ser Ala Val Glu Val Gln Cys Ile Ala Thr Pro Ala Asp Pro Thr Asp
            180                 185                 190

Pro Leu Leu Arg Arg Trp Thr Lys His Pro Ala Asn Pro Val Ile Trp
        195                 200                 205

Ser Pro Pro Gly Val Gly Thr Lys Asp Phe Arg Asp Pro Met Thr Ala
210                 215                 220

Trp Tyr Asp Glu Ser Asp Asp Thr Trp Arg Thr Leu Leu Gly Ser Lys
225                 230                 235                 240

Asp Asp Asn Asn Gly His His Asp Gly Ile Ala Met Met Tyr Lys Thr
                245                 250                 255

Lys Asp Phe Leu Asn Tyr Glu Leu Ile Pro Gly Ile Leu His Arg Val
            260                 265                 270

Glu Arg Thr Gly Glu Trp Glu Cys Ile Asp Phe Tyr Pro Val Gly Arg
        275                 280                 285

Arg Thr Ser Asp Asn Ser Ser Glu Met Leu His Val Leu Lys Ala Ser
    290                 295                 300

Met Asp Asp Glu Arg His Asp Tyr Tyr Ser Leu Gly Thr Tyr Asp Ser
305                 310                 315                 320

Ala Ala Asn Arg Trp Thr Pro Ile Asp Pro Glu Leu Asp Leu Gly Ile
                325                 330                 335

Gly Leu Arg Tyr Asp Trp Gly Lys Phe Tyr Ala Ser Thr Ser Phe Tyr
            340                 345                 350

Asp Pro Ala Lys Lys Arg Arg Val Leu Met Gly Tyr Val Gly Glu Val
        355                 360                 365

Asp Ser Lys Arg Ala Asp Val Val Lys Gly Trp Ala Ser Ile Gln Ser
    370                 375                 380

Val Pro Arg Thr Ile Ala Leu Asp Glu Lys Thr Arg Thr Asn Leu Leu
385                 390                 395                 400

Leu Trp Pro Val Glu Glu Ile Glu Thr Leu Arg Leu Asn Ala Thr Glu
                405                 410                 415

Leu Ser Asp Val Thr Leu Asn Thr Gly Ser Val Ile His Ile Pro Leu
            420                 425                 430

Arg Gln Gly Thr Gln Leu Asp Ile Glu Ala Thr Phe His Leu Asp Ala
        435                 440                 445

Ser Ala Val Ala Ala Leu Glu Ala Asp Val Gly Tyr Asn Cys Ser
    450                 455                 460

Ser Ser Gly Gly Ala Val Asn Arg Gly Ala Leu Gly Pro Phe Gly Leu
465                 470                 475                 480
```

```
Leu Val Leu Ala Ala Gly Asp Arg Arg Gly Glu Gln Thr Ala Val Tyr
                485                 490                 495

Phe Tyr Val Ser Arg Gly Leu Asp Gly Leu His Thr Ser Phe Cys
            500                 505                 510

Gln Asp Glu Leu Arg Ser Ser Arg Ala Lys Asp Val Thr Lys Arg Val
            515                 520                 525

Ile Gly Ser Thr Val Pro Val Leu Asp Gly Glu Ala Phe Ser Met Arg
            530                 535                 540

Val Leu Val Asp His Ser Ile Val Gln Gly Phe Ala Met Gly Gly Arg
545                 550                 555                 560

Thr Thr Met Thr Ser Arg Val Tyr Pro Met Glu Ala Tyr Gln Glu Ala
                565                 570                 575

Lys Val Tyr Leu Phe Asn Asn Ala Thr Gly Ala Ser Val Thr Ala Glu
            580                 585                 590

Arg Leu Val Val His Glu Met Asp Ser Ala His Asn Gln Leu Ser Asn
            595                 600                 605

Met Asp Asp His Ser Tyr Val Gln
            610                 615

<210> SEQ ID NO 2
<211> LENGTH: 662
<212> TYPE: PRT
<213> ORGANISM: Triticum aestivum

<400> SEQUENCE: 2

Met Asp Ser Ser Arg Val Ile Leu Ile Pro Gly Thr Pro Pro Leu Pro
1               5                   10                  15

Tyr Ala Tyr Glu Gln Leu Pro Ser Ser Ala Asp Ala Lys Gly Ile
            20                  25                  30

Glu Glu Glu Arg Ala Gly Gly Gly Leu Arg Trp Arg Ala Cys Ala
            35                  40                  45

Ala Val Leu Ala Ala Ser Ala Val Val Ala Leu Val Val Ala Ala Ala
        50                  55                  60

Val Phe Gly Ala Ser Gly Ala Gly Trp Asp Ala Val Ala Ala Ser Val
65                  70                  75                  80

Pro Ala Thr Pro Ala Thr Glu Phe Pro Arg Ser Arg Gly Lys Glu His
                85                  90                  95

Gly Val Ser Glu Lys Thr Ser Gly Ala Tyr Ser Ala Asn Ala Phe Pro
            100                 105                 110

Trp Ser Asn Ala Met Leu Gln Trp Gln Arg Thr Gly Tyr His Phe Gln
        115                 120                 125

Pro Asp Lys Tyr Tyr Gln Asn Asp Pro Asn Gly Pro Val Tyr Tyr Gly
        130                 135                 140

Gly Trp Tyr His Phe Phe Tyr Gln Tyr Asn Pro Ser Gly Ser Val Trp
145                 150                 155                 160

Glu Pro Gln Ile Val Trp Gly His Ala Val Ser Lys Asp Leu Ile His
                165                 170                 175

Trp Arg His Leu Pro Pro Ala Leu Val Pro Asp Gln Trp Tyr Asp Ile
            180                 185                 190

Lys Gly Val Leu Thr Gly Ser Ile Thr Val Leu Pro Asp Gly Lys Val
        195                 200                 205

Ile Leu Leu Tyr Thr Gly Asn Thr Glu Thr Phe Ala Gln Val Thr Cys
        210                 215                 220

Leu Ala Glu Pro Ala Asp Pro Ser Asp Pro Leu Leu Arg Glu Trp Val
225                 230                 235                 240
```

-continued

```
Lys His Pro Ala Asn Pro Val Val Phe Pro Pro Gly Ile Gly Met
                245                 250                 255
Lys Asp Phe Arg Asp Pro Thr Thr Ala Trp Phe Asp Glu Ser Asp Gly
            260                 265                 270
Thr Trp Arg Thr Ile Ile Gly Ser Lys Asn Asp Ser Asp His Ser Gly
        275                 280                 285
Ile Val Phe Ser Tyr Lys Thr Lys Asp Phe Leu Ser Tyr Glu Leu Met
    290                 295                 300
Pro Gly Tyr Met Tyr Arg Gly Pro Lys Gly Thr Gly Glu Tyr Glu Cys
305                 310                 315                 320
Ile Asp Leu Tyr Ala Val Gly Gly Arg Lys Ala Ser Asp Met Tyr
                325                 330                 335
Asn Ser Thr Ala Glu Asp Val Leu Tyr Val Leu Lys Glu Ser Ser Asp
                340                 345                 350
Asp Asp Arg His Asp Trp Tyr Ser Leu Gly Arg Phe Asp Ala Ala Ala
            355                 360                 365
Asn Lys Trp Thr Pro Ile Asp Glu Glu Leu Glu Leu Gly Val Gly Leu
        370                 375                 380
Arg Tyr Asp Trp Gly Lys Tyr Tyr Ala Ser Lys Ser Phe Tyr Asp Pro
385                 390                 395                 400
Val Lys Lys Arg Arg Val Val Trp Ala Tyr Val Gly Glu Thr Asp Ser
                405                 410                 415
Glu Arg Ala Asp Ile Thr Lys Gly Trp Ala Asn Leu Gln Ser Ile Pro
            420                 425                 430
Arg Thr Val Glu Leu Asp Glu Lys Thr Arg Thr Asn Leu Val Gln Trp
        435                 440                 445
Pro Val Glu Glu Leu Asp Ala Leu Arg Ile Asn Thr Thr Asp Leu Ser
    450                 455                 460
Gly Ile Thr Val Gly Ala Gly Ser Val Ala Phe Leu Pro Leu His Gln
465                 470                 475                 480
Thr Ala Gln Leu Asp Ile Glu Ala Thr Phe Arg Ile Asp Ala Ser Ala
                485                 490                 495
Ile Glu Ala Leu Asn Glu Ala Asp Val Ser Tyr Asn Cys Thr Thr Ser
            500                 505                 510
Ser Gly Ala Ala Thr Arg Gly Ala Leu Gly Pro Phe Gly Leu Leu Val
        515                 520                 525
Leu Ala Asn Arg Ala Leu Thr Glu Gln Thr Gly Val Tyr Phe Tyr Val
    530                 535                 540
Ser Lys Gly Leu Asp Gly Gly Leu Arg Thr His Phe Cys His Asp Glu
545                 550                 555                 560
Leu Arg Ser Ser His Ala Ser Asp Val Val Lys Arg Val Val Gly Ser
                565                 570                 575
Thr Val Pro Val Leu Asp Gly Glu Asp Phe Ser Val Arg Val Leu Val
            580                 585                 590
Asp His Ser Ile Val Gln Ser Phe Ala Met Gly Gly Arg Leu Thr Ala
        595                 600                 605
Thr Ser Arg Ala Tyr Pro Thr Glu Ala Ile Tyr Ala Ala Ala Gly Val
    610                 615                 620
Tyr Met Phe Asn Asn Ala Thr Gly Thr Ser Val Thr Ala Glu Lys Leu
625                 630                 635                 640
Val Val His Asp Met Asp Ser Ser Tyr Asn His Ile Tyr Thr Asp Asp
                645                 650                 655
```

Asp Leu Val Val Val Asp
    660

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Artificial forward primer.
<221> NAME/KEY: misc_feature
<222> LOCATION: 14
<223> OTHER INFORMATION: n can be one of a,t,c, or g

<400> SEQUENCE: 3
atgaatcgat cccnaatcgg                                              20

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Artificial reverse primer.
<221> NAME/KEY: misc_feature
<222> LOCATION: 3,6
<223> OTHER INFORMATION: n can be one of a,t,c,g

<400> SEQUENCE: 4
ccngtngcag ttagttagaa                                              20

<210> SEQ ID NO 5
<211> LENGTH: 1851
<212> TYPE: DNA
<213> ORGANISM: Triticum aestivum
<220> FEATURE:
<221> NAME/KEY: misc_feature
<222> LOCATION: (1)..(1851)
<223> OTHER INFORMATION: cDNA

<400> SEQUENCE: 5
atggggtcac acggcaagcc accgctaccg tacgcgtaca agccactgcc ctccgacgcc       60
gacggcgagc gggccggctg cacgaggtgg cgcgtgtgcg ccgtcgcgct gacggcctcg      120
gccatggtgg tggtggtggt cggcgccacg ctcctggcag ggttccgggt ggaccaggcc      180
gtcgacgagg aggcggcggg cgggttcccg tggagcaacg agatgctgca gtggcagcgc      240
agtggctacc atttccagac ggccaagaac tacatgagcg atcccaacgg tctgatgtac      300
taccgtggat ggtaccacat gttcttccag tacaacccgg tgggcaccga ctgggacgac      360
ggcatggagt ggggccacgc cgtgtcccgg aacctcgtcc aatggcgcac cctccctatt      420
gccatggtgg ccgaccagtg gtacgacatc ctcggggttc tatcgggctc tatgaccgtg      480
ctacccaatg gcacggtcat catgatctac acggggggcca ccaacgcctc cgccgttgag      540
gtccagtgca tcgccactcc cgccgaccct accgacccc tcctccgccg ctggaccaag      600
caccccgcca acccgtcat ctggtcgccg ccggggggtcg gcaccaagga tttccgagac      660
ccgatgaccg cttggtacga tgaatctgat gacacatggc gcaccctgct cgggtccaag      720
gacgacaaca acggccacca cgatggcatc gccatgatgt acaagaccaa ggacttcctt      780
aactacgagc tcatcccggg catcttgcat cgggtcgagc gcaccggcga gtgggagtgc      840
atcgacttct accctgtcgg tcgccgcacc agcgacaact catcggagat gttgcacgtg      900

-continued

| | |
|---|---|
| ttgaaggcga gcatggacga cgaacggcat gactactact cgctaggcac gtacgactct | 960 |
| gcggcaaaca ggtggacgcc gatcgacccg gagctcgact tggggatcgg gttgagatac | 1020 |
| gactggggta agttctacgc gtccacctcg ttctatgatc cggcgaagaa gcgacgcgtg | 1080 |
| ctgatggggt acgtcggcga ggtcgactcc aagcgggctg atgtggtgaa gggatgggcc | 1140 |
| tcaattcagt cagttccaag gacaattgct ctcgacgaga agacccggac gaacctcctc | 1200 |
| ctctggcccg tggaggagat tgagaccctc cgcctcaacg ccaccgaact cagcgacgtc | 1260 |
| acccttaaca ccggctccgt catccatatc ccgctccgcc aaggcactca gctcgacatc | 1320 |
| gaggccactt tccaccttga tgcttctgcc gtcgctgccc tcaatgaggc cgatgtgggc | 1380 |
| tacaactgca gcagcagcgg cggtgctgtt aaccgcggcg cgctaggccc cttcggcctc | 1440 |
| ctcgtcctcg ctgccggtga ccgccgtggc gagcaaacgg cggtgtactt ctacgtgtcc | 1500 |
| aggggggctcg acggaggcct ccataccagc ttctgccaag acgagttacg gtcgtcacgg | 1560 |
| gccaaggacg tgacgaagcg agtgattggg agcacggtgc cggtgctcga cggcgaggct | 1620 |
| ttctcgatga gggtgctcgt ggaccactcc atcgtgcagg gcttcgcgat gggcgggagg | 1680 |
| accacgatga cgtcacgggt gtacccgatg gaggcctatc aggaggcaaa agtgtacttg | 1740 |
| ttcaacaatg ccaccggtgc cagcgtcacg gcggaaaggc tcgtcgtgca cgagatggac | 1800 |
| tcagcgcaca accagctctc caatatggac gatcactcgt atgttcaatg a | 1851 |

<210> SEQ ID NO 6
<211> LENGTH: 1989
<212> TYPE: DNA
<213> ORGANISM: Triticum aestivum
<220> FEATURE:
<221> NAME/KEY: misc_feature
<222> LOCATION: (1)..(1989)
<223> OTHER INFORMATION: cDNA

<400> SEQUENCE: 6

| | |
|---|---|
| atggattcgt ctcgcgtcat actcatcccc ggcacgccgc cgctgccgta cgcctacgag | 60 |
| cagctgccgt cctcctccgc ggacgccaag ggcatcgagg aggagcgggc cggcggcggt | 120 |
| ggcctgaggt ggcgcgcgtg cgccgccgtg ctggccgcct cggccgtggt ggcgctcgtc | 180 |
| gtcgccgccg cggtcttcgg ggccagcggg gcgggctggg acgcggtggc cgcctccgtg | 240 |
| ccggcgaccc cggcgacgga gttcccgagg agcaggggca aggagcacgg cgtgtcggag | 300 |
| aagacgtcgg gggcctactc cgccaacgcg ttcccgtgga gcaacgccat gctgcagtgg | 360 |
| cagcgcaccg gctaccattt ccagccggac aagtactacc agaacgatcc caacggtccg | 420 |
| gtttactatg cggatggta ccacttcttc taccagtaca acccgtcggg ctccgtgtgg | 480 |
| gagccccaaa tcgtgtgggg ccacgccgtg tccaaggacc tcattcactg cgccacctc | 540 |
| ccgccggcct tggtgcccga ccagtggtac gacatcaagg gcgtcctcac cggctccatc | 600 |
| accgtgctcc ccgacggcaa ggtcatcctc ctctacacgg ggaacaccga acctttgcg | 660 |
| caggtgacct gcctcgcgga gcccgccgac ccgagcgatc ccctcctccg gagtgggtc | 720 |
| aagcaccccg ccaaccccgt cgtgttcccg ccccccggca tcggcatgaa ggacttccgc | 780 |
| gaccccacca ccgcgtggtt cgacgagtcc gacggcacgt ggcgcaccat catcggctcc | 840 |
| aagaacgact cggaccactc cggcatcgtc ttctcctaca agaccaagga cttcctcagc | 900 |
| tacgagctga tgccggggta catgtaccgc ggccccaagg gcaccggcga gtacgagtgc | 960 |
| atcgacctct acgccgtcgg cggggggccgc aaggccagcg acatgtacaa ctcgaccgcc | 1020 |
| gaggacgtgc tgtacgtgct caaggagagc agcgacgacg accggcacga ctggtactcg | 1080 |

```
ctgggccggt tcgacgccgc cgccaacaag tggacgccga tcgacgagga gctggagctc    1140
ggcgtcgggc tgcggtacga ctggggcaag tactacgcgt ccaagtcctt ctacgacccc    1200
gtgaagaagc ggcgcgtcgt gtgggcgtac gtcggcgaga ccgactcgga gcgcgccgac    1260
atcaccaagg ggtgggccaa cctccagtcg attccgagga cagtggagct tgacgagaag    1320
acccggacga acctcgtcca atggcctgtg gaggagctcg atgccctccg catcaacacc    1380
accgatctca gcggcatcac cgtcggcgcc ggctccgttg ccttcctccc cctccatcag    1440
accgctcagc tcgacatcga ggcaaccttc cgcatcgatg cctccgccat tgaggccctc    1500
aacgaggccg atgttagcta caactgcacc accagcagcg gggctgccac ccgcggcgcg    1560
cttggcccct tcggcctcct tgtcctcgcc aaccgcgccc tgaccgaaca gacgggagtg    1620
tacttctatg tgtccaaggg cctcgacggt ggtcttcgga ctcacttctg ccacgacgag    1680
ttgcgctcgt cgcatgctag tgacgtggtg aagcgggtgg tgggtagcac ggtgccagtg    1740
ctcgacggcg aagatttttc cgttagggtg ctcgtggacc actccattgt gcagagcttc    1800
gcgatgggcg ggaggttgac agcaacgtcg agggcgtacc cgaccgaggc catctacgcg    1860
gcagcggggg tctacatgtt caacaacgcc accggcacta gcgtcaccgc cgagaagctt    1920
gtcgtgcatg atatggactc gtcgtacaac catatataca cagatgatga cttggtagtc    1980
gtcgattag                                                           1989
```

The advantages of the present invention may be concluded as follows.

1) With the use of the present invention, it has become possible to provide i) a novel wheat-derived sucrose:fructan 6-fructosyltransferase cDNA encoding different amino acid sequence from that of a conventional sucrose:fructan 6-fructosyltransferase cDNA, and ii) a novel wheat-derived invertase cDNA encoding different amino acid sequence from that of a conventional invertase cDNA.

2) Since the novel wheat-derived sucrose:fructan 6-fructosyltransferase cDNA and the novel wheat-derived invertase cDNA of the present invention are all capable of expressing at a low temperature environment so as to produce (synthesize) a desired fructan in a low temperature environment. Therefore, when either or both of the cDNAs of the present invention are introduced into a plant, it is sure to efficiently increase the cold resistance of the plant, thereby making it possible to produce new plant variety having an increased cold resistance.

Further, since the novel wheat-derived sucrose:fructan 6-fructosyltransferase cDNA and the novel wheat-derived invertase cDNA of the present invention are all capable of synthesizing a desired fructan, these cDNAs are useful for industrially producing a fructo-oligosaccharide which can be used to prevent a carious tooth and for increasing intestinal bifid bacteria.

While the presently preferred embodiments of the this invention have been shown and described above, it is to be understood that these disclosures are for the purpose of illustration and that various changes and modifications may be made without departing from the scope of the invention as set forth in the appended claims.

What is claimed is:

1. The wheat-derived sucrose:fructan 6-fructosyltransferase cDNA, wherein said cDNA encodes a fructan synthesizing enzyme active at low temperatures.

2. A plant transformed with a cDNA according to claim 1.

3. A micro-organism transformed with a cDNA according to claim 1.

4. A micro-organism according to claim 3 which is a yeast.

* * * * *